United States Patent
Onuma (10) Patent No.: US 11,585,803 B2
(45) Date of Patent: Feb. 21, 2023

(54) ANALYSIS METHOD AND ANALYSIS SYSTEM

(71) Applicant: ARKRAY, Inc., Kyoto (JP)

(72) Inventor: Naotsugu Onuma, Kyoto (JP)

(73) Assignee: ARKRAY, INC., Kyoto (JP)

( * ) Notice: Subject to any disclaimer, the term of this patent is extended or adjusted under 35 U.S.C. 154(b) by 199 days.

(21) Appl. No.: 16/504,928

(22) Filed: Jul. 8, 2019

(65) Prior Publication Data
US 2020/0011850 A1    Jan. 9, 2020

(30) Foreign Application Priority Data

Jul. 9, 2018  (JP) .............................. JP2018-130184
Jun. 24, 2019  (JP) .............................. JP2019-116669

(51) Int. Cl.
*G01N 33/487* (2006.01)
*G01N 27/447* (2006.01)

(52) U.S. Cl.
CPC .  *G01N 33/48707* (2013.01); *G01N 27/44704* (2013.01); *G01N 27/44756* (2013.01)

(58) Field of Classification Search
CPC ........ G01N 27/44791; G01N 33/48707; B01L 3/5027
See application file for complete search history.

(56) References Cited

U.S. PATENT DOCUMENTS 8,080,144 B2 * 12/2011 Ross ..................... B01D 57/02
                                                   204/549
2003/0057092 A1    3/2003 Chien et al.
2004/0018638 A1 *  1/2004 Shoji ................ G01N 27/44713
                                                   436/516
2005/0161326 A1    7/2005 Morita et al.
2012/0037508 A1    2/2012 Shiraki et al.
(Continued)

FOREIGN PATENT DOCUMENTS

JP    2010-054195 A    3/2010
JP    2016-057289 A    4/2016

OTHER PUBLICATIONS

D. Harvey, 12.8: Electrophoresis, p. 1-11. (Year: 2022).*
(Continued)

*Primary Examiner* — Luan V Van
*Assistant Examiner* — Caitlyn Mingyun Sun
(74) *Attorney, Agent, or Firm* — Morgan, Lewis & Bockius LLP (57) ABSTRACT

An analysis method using a microchip which is provided with a capillary flow path, and a sample reservoir connected to the capillary flow path, in which the capillary flow path is filled with a first liquid for electrophoresis, and a second liquid containing a sample is stored in the sample reservoir, and including a pressurization process in which the first liquid is pressurized into the capillary flow path from a side of the capillary flow path that is opposite from the side connected to the sample reservoir, and a separation process in which a voltage is applied between the sample reservoir storing the second liquid and the capillary flow path filled with the first liquid, such that components in the sample contained in the second liquid move in the capillary flow path and the components are separated in the capillary flow path.

18 Claims, 8 Drawing Sheets

(56) References Cited

U.S. PATENT DOCUMENTS

2012/0234678 A1* 9/2012 Diller .................. C07K 1/26
                                                  436/15
2015/0136604 A1* 5/2015 Nielsen ............... B01F 33/452
                                                  204/453
2017/0168013 A1* 6/2017 Shigemitsu ....... B01L 3/502715

OTHER PUBLICATIONS

Extended European Search Report issued in corresponding European Patent Application No. 19184525.4 dated Nov. 26, 2019.
Office Action dated Sep. 20, 2022, issued in corresponding Japanese Patent Application No. 2019-116669.
Office Action dated Oct. 18, 2022, issued in corresponding European Patent Application No. 19184525.4.

* cited by examiner

EXAMPLE 1

Fig.6B

EXAMPLE 2

Fig.6C

COMPARATIVE EXAMPLE 1

ANALYSIS METHOD AND ANALYSIS SYSTEM

CROSS-REFERENCE TO RELATED APPLICATION

This application claims priority under 35 USC 119 from Japanese Patent Application No. 2018-130184 and Japanese Patent Application No. 2019-116669, the disclosure of which is incorporated by reference herein.

All publications, patent applications, and technical standards mentioned in this specification are herein incorporated by reference to the same extent as if each individual publication, patent application, or technical standard was specifically and individually indicated to be incorporated by reference.

BACKGROUND

Technical Field

The present invention relates to an analysis method and an analysis system.

Related Art

In the field of clinical tests, specimen analysis by capillary electrophoresis has conventionally been conducted. In recent years, specimen analysis by electrophoresis using a microchip has been conducted in order to miniaturize and simplify an apparatus. For example, the microchip includes a capillary tube, holding tanks for holding various liquids, etc.

For example, when blood proteins such as hemoglobin are analyzed by electrophoresis using a microchip, the capillary tube is irradiated with light and the light transmitted through the capillary tube is detected and the sample moving in the capillary tube is analyzed. In addition, from the viewpoint of enhancing the analysis accuracy on the sample, a method has been proposed by which the capillary tube is filled with a electrophoresis liquid, and the sample is fed into a feed tank connected with the capillary tube and made to flow inside the feed tank so as to generate a shear flow in the connecting portion between the capillary tube and the feed tank to form an interface between the sample and the electrophoresis liquid at the connecting portion (see, for example, Patent Document 1).

RELATED ART DOCUMENTS

Patent Documents

Patent Document 1 Japanese Patent Application Laid-Open (JP-A) No. 2016-057289

SUMMARY

Object of the Invention

For example, when the capillary tube is filled with an electrophoresis liquid, and a sample is introduced into the feed tank connected to the capillary tube, part of the sample introduced into the feed tank may move into the capillary tube, and sometimes the interface between the sample and the electrophoresis liquid may not be formed well. In such an event, if an analysis of the sample is performed by electrophoresis, the analysis accuracy with respect to the sample may be deteriorated.

An object of the present invention is to provide an analysis method and an analysis system which are superior in analysis accuracy with respect to the sample.

Means for Solving the Problem

A specific means for achieving the object is, for example, as follows.

<1> An analysis method using a microchip that is provided with a capillary flow path and a sample reservoir connected to the capillary flow path, in which the capillary flow path is filled with a first liquid for electrophoresis, and a second liquid containing a sample is stored in the sample reservoir, the analysis method comprising:

a pressurization process in which the first liquid is pressurized into the capillary flow path from a side of the capillary flow path that is opposite from a side connected to the sample reservoir; and a separation process in which, after the pressurization process, a voltage is applied between the sample reservoir storing the second liquid and the capillary flow path filled with the first liquid, such that components in the sample contained in the second liquid move in the capillary flow path and the components are separated in the capillary flow path.

<2> The analysis method according to <1>, further comprising, before the pressurization process, a confirmation process of confirming continuity between the capillary flow path filled with the first liquid and the sample reservoir storing the second liquid by applying a voltage between the sample reservoir and the capillary flow path, wherein, in the confirmation process, components in the sample contained in the second liquid move in the capillary flow path.

<3> The analysis method according to <1> or <2>, further comprising:

a filling process of filling the capillary flow path with the first liquid; and a supply process of supplying the second liquid to the sample reservoir after the filling process and before the pressurization process.

<4> The analysis method according to any one of <1> to <3>, wherein an interface between the first liquid and the second liquid is formed in a connecting portion between the capillary flow path and the sample reservoir by pressurizing the first liquid into the capillary flow path in the pressurization process.

<5> The analysis method according to any one of <1> to <4>, further comprising a waiting process of waiting for a predetermined time after the pressurization process and before the separation process.

<6> An analysis system comprising:

an arrangement unit in which a microchip provided with a capillary flow path and a sample reservoir connected to the capillary flow path is arranged;

a filling means for filling the capillary flow path in the microchip arranged in the arrangement unit with a first liquid for electrophoresis;

a supply means for supplying a second liquid containing a sample into the sample reservoir in the microchip arranged in the arrangement unit;

a control unit for controlling pressurization of the first liquid into the capillary flow path from a side of the capillary flow path that is opposite from a side connected to the sample reservoir, the pressurization being conducted after the filling with the first liquid by the filling means and after the supply of the second liquid by the supply means; and a separation means by which, after pressurizing the first liquid into the capillary flow path, a voltage is applied between the sample reservoir storing the second liquid and the capillary flow path filled with the first liquid, such that components in the sample contained in the second liquid move through the capillary flow path and the components are separated in the capillary flow path.

Effect of the Invention

According to an aspect of the present invention, it is possible to provide an analysis method and an analysis system that excel in the analysis accuracy with respect to the sample.

DETAILED DESCRIPTION OF THE INVENTION

An analysis method, and an analysis system of an aspect of the invention will be described below.

Herein, the numerical range expressed by using "to" means a range including numerical values described before and after "to" as a lower limit value and an upper limit value.

[Analysis Method]

The analysis method according to an aspect of the present invention uses a microchip provided with a capillary flow path, and a sample reservoir connected to the capillary flow path, in which the capillary flow path is filled with a first liquid for electrophoresis, and a second liquid containing a sample is stored in the sample reservoir, and includes a pressurization process in which the first liquid is pressurized into the capillary flow path from a side of the capillary flow path that is opposite from a side connected to the sample reservoir, and a separation process in which a voltage is applied between the sample reservoir storing the second liquid and the capillary flow path filled with the first liquid, such that components in the sample contained in the second liquid move in the capillary flow path and the components are separated in the capillary flow path.

When a component in a sample is analyzed by electrophoresis using a microchip, for the sake of realizing a stable measurement operation it is conceivable that the continuity from the sample reservoir to the end of the capillary flow path that is opposite from the side connected to the sample reservoir is confirmed by applying a voltage. However, when the continuity is confirmed by applying a voltage, electrophoresis is inevitably enforced in the capillary flow path, and thereafter until the voltage application is terminated after an elapse of a predetermined time, mixing occurs at the interface between the first liquid, which is the electrophoresis liquid, and the second liquid containing the sample to blur the interface. Then, the analysis of the sample by electrophoresis is performed after an elapse of a predetermined time, and therefore the analyte component is not separated favorably causing various problems that the analyte component cannot be detected accurately discriminated from other components, the component ratio cannot be determined accurately, or the like, which may deteriorate the analysis accuracy with respect to the sample.

Further, when the capillary flow path is filled with the first liquid, and then the second liquid containing the sample is supplied into the sample reservoir connected to the capillary flow path, part of the second liquid stored in the sample reservoir may be moved into the capillary flow path due to the momentum of the supplied second liquid, the direction of such second liquid, etc. and there is a risk that an interface between the first liquid and the second liquid may not be formed favorably. In such an event, if an analysis of the sample is performed by electrophoresis, the aforedescribed analysis accuracy with respect to the sample may be deteriorated.

On the other hand, in the analysis method of this aspect, a microchip in which the capillary flow path is filled with the first liquid, and the second liquid containing the sample is stored in the sample reservoir is used, a pressurization process of pressing the first liquid in the capillary flow path is performed, and after the pressurization process a separation process of separating the components in the capillary flow path is performed. Accordingly, the analysis method of this aspect is superior in the analysis accuracy with respect to the sample. This is presumably because by pressurizing the first liquid in the capillary flow path the second liquid having moved into the capillary flow path is pushed back toward the sample reservoir to form an interface between the first liquid and the second liquid containing the sample at the connecting portion between the capillary flow path and the sample reservoir; and when a voltage is applied in a state where the interface has been formed, the sample can be analyzed with high accuracy. By adopting the analysis method of the aspect, even if the continuity is confirmed by applying a voltage as described above, the analysis accuracy with respect to the sample can be superior, so that a simple continuity confirmation method and high analysis accuracy with respect to the sample can be obtained at the same time.

In the analysis method of this disclosure, it may be sometimes difficult to control such that only the second liquid having moved into the capillary flow path is sent back to the sample reservoir without sending the first liquid in the capillary flow path to the sample reservoir. In this case, the second liquid and the first liquid near the boundary are both sent back toward the sample reservoir. However, since the volume of the capillary flow path is very small compared to the volume of the sample reservoir, only a very small amount of the first liquid is transferred to the sample reservoir. The very small amount of the first liquid transferred to the sample reservoir is diluted by the large amount of the second liquid present in the sample reservoir. Further, since the volume of the capillary flow path is very small, and the fluid flow from the capillary flow path to the sample reservoir by pressurization remains, the second liquid present in the sample reservoir does not move to the capillary flow path, and an interface between the first liquid and the second liquid can be formed at the opening of the capillary flow path in the connecting portion between the sample reservoir and the capillary flow path.

A microchip used in the analysis method of the aspect is used for analysis of substances (preferably biologically derived substances) in a sample by capillary electrophoresis.

Examples of a sample used by the analysis method of this aspect include a specimen derived from a living organism, a specimen derived from the environment, a metal, a chemical substance, and a pharmaceutical. The specimen derived from a living organism is not particularly limited, and examples thereof include urine, blood, hair, saliva, sweat, and nail. Examples of the blood specimen include a red blood cell, whole blood, serum, and plasma. Examples of the living organism include a human, a non-human animal, and a plant, and examples of the non-human animal include a mammal other than humans, an amphibian reptile, a fish, a shellfish, and an insect. The specimen derived from the environment is not particularly limited, and examples thereof include food, water, soil, atmosphere, and air. Examples of the food include a fresh food, and a processed food. Examples of the water include drinking water, groundwater, river water, sea water, and domestic wastewater. The sample is preferably blood collected from a human body or the like.

In addition, a component which is included in a sample and which is a target component of the analysis method of this aspect (hereinafter, also referred to as a "component included in a sample"), is preferably a biologically derived substance. Among the biologically derived substances, hemoglobin is more preferable.

More specifically, preferably the sample is blood, and the component contained in the sample is a biologically derived substance, and more preferably the sample is blood, and the component contained in the sample is hemoglobin.

Further, for example, a sample may be suspended, dispersed, or dissolved in a diluent described later to prepare a liquid, which may be used as the second liquid.

Examples of a components which is contained in the blood and to be analyzed by the analysis method of this aspect include hemoglobin (Hb), albumin (A1b), globulin ($\alpha$1, $\alpha$2, $\beta$, and $\gamma$ globulins), and fibrinogen. Examples of hemoglobin include normal hemoglobin (HbA0), glycated hemoglobin, modified hemoglobin, fetal hemoglobin (HbF), and mutated hemoglobin. Examples of glycated hemoglobin include hemoglobin A1a (HbA1a), hemoglobin A1b (HbA1b), hemoglobin A1c (HbA1c), hemoglobin A1d1 (HbA1d1), Hemoglobin A1d2 (HbA1d2), hemoglobin A1d3 (HbA1d3), hemoglobin A1e (HbA1e), and GHbLys. Examples of hemoglobin A1c include stable HbA1c (S-HbA1c), and labile HbA1c (L-HbA1c). Examples of modified hemoglobin include carbamylated Hb, and acetylated H1b. Examples of mutated hemoglobin include hemoglobin C (HbC), hemoglobin D (HbD), hemoglobin E (HbE), and hemoglobin S (HbS).

Figure 1:
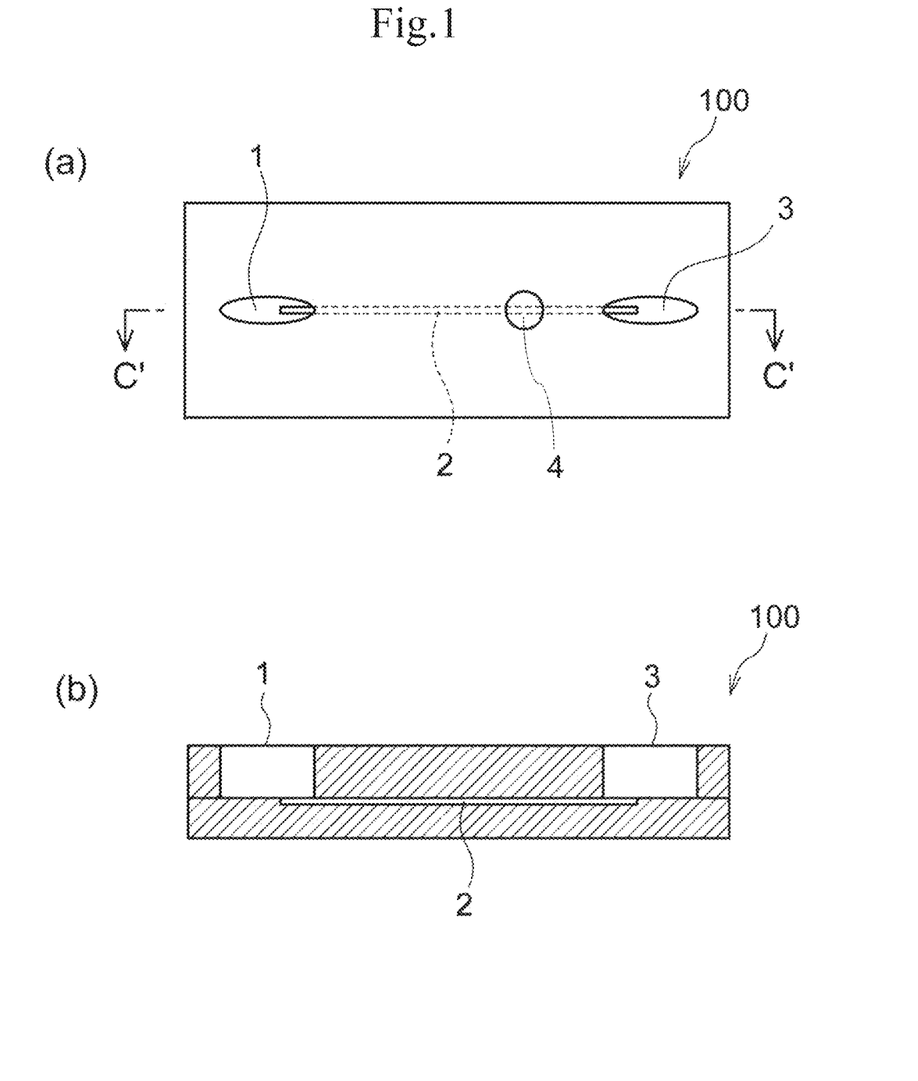
FIG. 1 shows schematic configuration diagrams of a microchip used in an analysis method and an analysis system of an aspect of the invention, and (a) is a top view, and (b) is a sectional view taken along the line C'-C' of (a).

The microchip used in the analysis method of the aspect will be described with reference to FIG. 1. FIG. 1 shows schematic configuration diagrams of a microchip used in an analysis method of an aspect of the invention, and (a) is a top view, (b) is a sectional view taken along the line C'-C' of (a). As shown in FIG. 1, a microchip 100 includes a sample reservoir 1, an electrophoresis liquid reservoir 3, a capillary flow path 2, and a detector 4. The microchip 100 may be manufactured, for example, by joining a pair of base materials, which are substantially rectangular plate-shaped members. More specifically, the microchip 100 may be manufactured by joining a base material having through holes corresponding to the sample reservoir 1 and the electrophoresis liquid reservoir 3, and a base material having a fine groove corresponding to the capillary flow path 2 in such a manner that each end of the groove faces a part of either of the two through holes.

Examples of the material of the base material constituting the microchip include glass, fused silica, and a resin, and from the viewpoints of cost, ease of processing, and ease of immobilization of a cationic polymer, a resin is preferable. Examples of the resin include an acrylic resin such as poly(methyl methacrylate) (PMMA), polycarbonate, poly (vinylidene chloride), cyclic polyolefin, poly(ether ether ketone), polystyrene, polytetrafluoroethylene (PTFE), cycloolefin, polypropylene, and polyethylene, and from the viewpoint of excellent light transmittance, poly(methyl methacrylate) is preferable.

As the microchip used in the analysis method of the aspect, a disposable type analysis chip which is not reused may be used.

The sample reservoir 1 is a tank that is supplied with a second liquid containing a component such as a biologically derived substance through an opening and stores the supplied second liquid. The sample reservoir 1 is connected to the end of the capillary flow path 2, and more specifically connected to the end of the capillary flow path 2 that is opposite from the side with the electrophoresis liquid reservoir 3.

There is no particular restriction on the second liquid insofar as it is a liquid including the above-described sample, and it may be the sample itself, or the sample diluted with a diluent.

The main agent of a diluent is not particularly limited, and examples thereof include water, and physiological saline, and a substance which can be contained in the first liquid for electrophoresis described below as a preferred example may be added to the diluent. For example, the diluent may be one obtained by adding a compound including a cathodic group to the main agent. Examples of the compound including a cathodic group include a cathodic group-containing polysaccharide, and more specific examples thereof include a sulfated polysaccharide, a carboxylated polysaccharide, a sulfonated polysaccharide, and a phosphorylated polysaccharide. As the carboxylated polysaccharide, alginic acid or a salt thereof (for example, sodium alginate) is preferable. As the sulfated polysaccharide, for example, chondroitin sulfate is preferable. There are seven kinds of chondroitin sulfate, namely A, B, C, D, E, H, and K, and any of them may be used. The concentration of a compound including a cathodic group (chondroitin sulfate) is preferably, for example, in the range of from 0.01% by mass to 5% by mass.

The electrophoresis liquid reservoir 3 is a tank to which a first liquid for electrophoresis is supplied through an opening, and which stores the supplied first liquid. The electrophoresis liquid reservoir 3 is connected to the end of the capillary flow path 2, more specifically connected to the end of the capillary flow path 2 that is opposite from the side with the sample reservoir 1. It is so configured that the first liquid stored in the electrophoresis liquid reservoir 3 is to fill the capillary flow path 2 by pressurization.

The first liquid which is an electrophoresis liquid used for electrophoresis is a medium which is supplied through the opening to the electrophoresis liquid reservoir 3 and fills the capillary flow path 2 to generate an electroosmotic flow in electrophoresis. The first liquid includes water, physiological saline, or the like. The first liquid preferably contains an acid. Examples of the acid include citric acid, maleic acid, tartaric acid, succinic acid, fumaric acid, phthalic acid, malonic acid, and malic acid. The first liquid preferably contains a weak base. Examples of the weak base include arginine, lysine, histidine, and a tris. The pH of the first liquid is preferably, for example, in the range of pH from 4.5 to 6. Examples of the buffer of the first liquid include MES, ADA, ACES, BES, MOPS, TES, and HEPES. The compound including a cathodic group described in the description of the diluent may also be added to the first liquid. The concentration of the compound including a cathodic group (chondroitin sulfate or the like) is preferably, for example, in the range of from 0.01% by mass to 5% by mass.

The capillary flow path 2 connects the sample reservoir 1 and the electrophoresis liquid reservoir 3, and is a flow path for analyzing a component in the second liquid supplied to the sample reservoir 1, and is more specifically a capillary tube for analyzing an analyte by electrophoresis.

The size of the capillary flow path 2 is not particularly limited, and preferably, for example, the depth is from 25 μm to 100 μm, the width is from 25 μm to 100 μm, and the length is from 5 mm to 150 mm.

From the viewpoint of enhancing the analytical performance, the capillary flow path 2 may be provided with an electric charge, for example, a positive electric charge on a wall face. The method of providing a positive charge is not particularly limited, and a cationic polymer may be immobilized in a region corresponding to the capillary flow path 2 in the above-described pair of base materials before joining the pair of base materials.

The detector 4 is for receiving and emitting light to be used in analysis when conducting an analysis by electrophoresis with the microchip 100, and is used, for example, for measuring absorbance. The detector 4 is formed at a position facing at least a portion of the capillary flow path 2. The position of the detector 4 may be appropriately determined according to the length of the capillary flow path 2 or the like.

Figure 4:
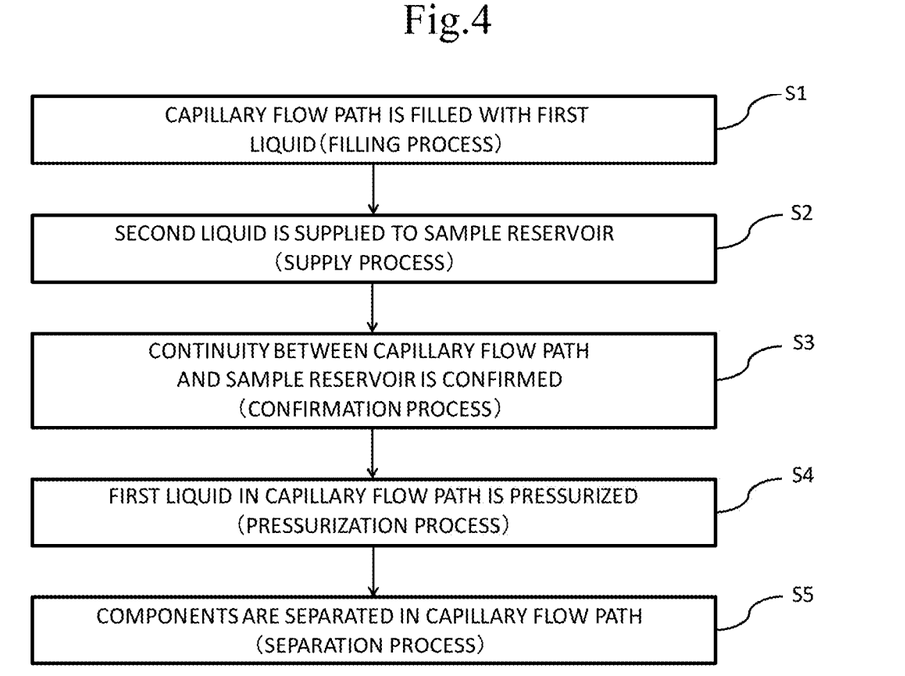
FIG. 4 is a flow chart showing the analysis method of a mode of the present invention.

Hereinafter, each process of the analysis method of the aspect using the above-described microchip 100 will be described with reference to FIG. 4. In this regard, the analysis method of the invention is not limited to one including all the following processes.

(Filling Process)

The analysis method of this aspect uses the microchip 100 and includes a filling process (S1) in which the capillary flow path 2 is filled with the first liquid. In the filling process (S1), for example, the first liquid is supplied to the electrophoresis liquid reservoir 3, and the first liquid stored in the electrophoresis liquid reservoir 3 may be pressurized to supply the first liquid to fill the capillary flow path 2.

(Supply Process)

The analysis method of this aspect includes a supply process (S2) of supplying the second liquid to the sample reservoir 1 after the filling process (S1). In the analysis method of the invention, a filling process of filling the capillary flow path with the first liquid may be performed after the supply process of supplying the second liquid to the sample reservoir.

(Confirmation Process)

The analysis method of the aspect includes after the supply process (S2) a confirmation process (S3) of confirming the continuity between the capillary flow path 2 filled with the first liquid and the sample reservoir 1 storing the second liquid by applying a voltage between the sample reservoir 1 and the capillary flow path 2. In the confirmation process (S3), the components in the sample contained in the second liquid move in the capillary flow path 2.

For example, in the confirmation process (S3), a voltage may be applied after the anode is brought into contact with the second liquid stored in the sample reservoir 1, and the cathode is brought into contact with the first liquid stored in the electrophoresis liquid reservoir 3. There is no particular restriction on the voltage to be applied, and it may be, for example, from 0.5 kV to 20 kV, from 0.5 kV to 10 kV, or from 0.5 kV to 5 kV. In this regard, in a case where it is confirmed that a predetermined current (for example, 5 μA or more) flows when the voltage within the above numerical range is applied, the confirmation process (S3) may be terminated.

Further, in the confirmation process (S3), a voltage may be applied after the cathode is brought into contact with the second liquid stored in the sample reservoir 1, and the anode is brought into contact with the first liquid stored in the electrophoresis liquid reservoir 3 allowing the components in the sample contained in the second liquid to move in the capillary flow path 2. In this case, it is preferable to use an alkaline solution containing a cationic polymer as the first liquid and the second liquid. As the alkaline solution containing a cationic polymer, for example, the alkaline solution containing a cationic polymer described in Japanese Patent No. 6052927 may be used.

After the confirmation process (S3), the second liquid stored in the sample reservoir may be made to flow by conducting once at least one of discharge and suction using a pump, or by repeating discharge and suction using a pump, as described later.

(Pressurization Process)

The analysis method of the aspect includes after the confirmation process (S3) a pressurization process (S4) of pressurizing the first liquid in the capillary flow path 2 from the side of the capillary flow path 2 that is opposite from the side connected to the sample reservoir 1. There is no particular restriction on the pressurization process (S4), insofar as, for example, it pressurizes the first liquid in the capillary flow path 2 from the side of the capillary flow path 2 that is opposite from the side connected to the sample reservoir 1, more specifically the first liquid may be resupplied into the capillary flow path 2 by pressurizing the first liquid stored in the electrophoresis liquid reservoir 3. The conditions for pressurizing the first liquid stored in the electrophoresis liquid reservoir 3 may be adjusted appropriately according to the voltage application condition in the confirmation process, the size of the capillary flow path 2, etc. For example, it may be pressurized at from 1 kPa to 20 kPa for from 0.1 sec to 5 sec. As for a pressurizing method, it may be a method by which the first liquid is pressurized by air pressure and sent into the capillary flow path 2, so as to send back the second liquid having moved into the capillary flow path 2 toward the sample reservoir 1.

(Separation Process)

Next, the analysis method of the aspect includes after the pressurization process (S4) a separation process (S5), by which a voltage is applied between the sample reservoir 1 storing the second liquid and the capillary flow path 2 filled with the first liquid such that the components in the sample contained in the second liquid move in the capillary flow path 2, and are separated in the capillary flow path 2.

For example, in the separation process (S5), a voltage may be applied after the anode is brought into contact with the second liquid stored in the sample reservoir 1, and the cathode is brought into contact with the first liquid stored in the electrophoresis liquid reservoir 3. As a result, an electroosmotic flow occurs in the capillary flow path 2, the second liquid is introduced from the sample reservoir 1 into the capillary flow path 2, and when the second liquid moves from the sample reservoir 1 toward the electrophoresis liquid reservoir 3, the components in the second liquid are separated. The applied voltage is preferably, for example, from 0.5 kV to 20 kV, more preferably from 0.5 kV to 10 kV, and still more preferably from 0.5 kV to 5 kV. As described above, a voltage may be applied after the cathode is brought into contact with the second liquid stored in the sample reservoir 1, and the anode is brought into contact with the first liquid stored in the electrophoresis liquid reservoir 3, and in this case it is preferable to use an alkaline solution containing a cationic polymer for the first liquid and the second liquid.

(Detection Process)

The analysis method of the present aspect may include a detection process of detecting a component separated in the capillary flow path. Detection of a separated component may be performed, for example, by an optical method such as absorbance measurement, and light may be emitted from the detector 4 and the absorbance may be measured. Also, the amount of change in absorbance per unit time may be determined from the measured absorbance.

In a case in which the component in the sample contained in the second liquid is hemoglobin, for example, it is preferable to measure the absorbance at a wavelength of 415 nm. The component ratio or the like in the second liquid may be obtained by calculating the peak height, the area of the peak, or the like of the electropherogram obtained by measuring the absorbance.

[Variation]

A variation of the analysis method of the aspect will be described. The variation of the analysis method is different from the aforedescribed analysis method of the aspect in that it includes a waiting process of waiting for a predetermined time after the pressurization process and before the separation process. Only the difference from the analysis method of the aspect will be described below.

Figure 5:
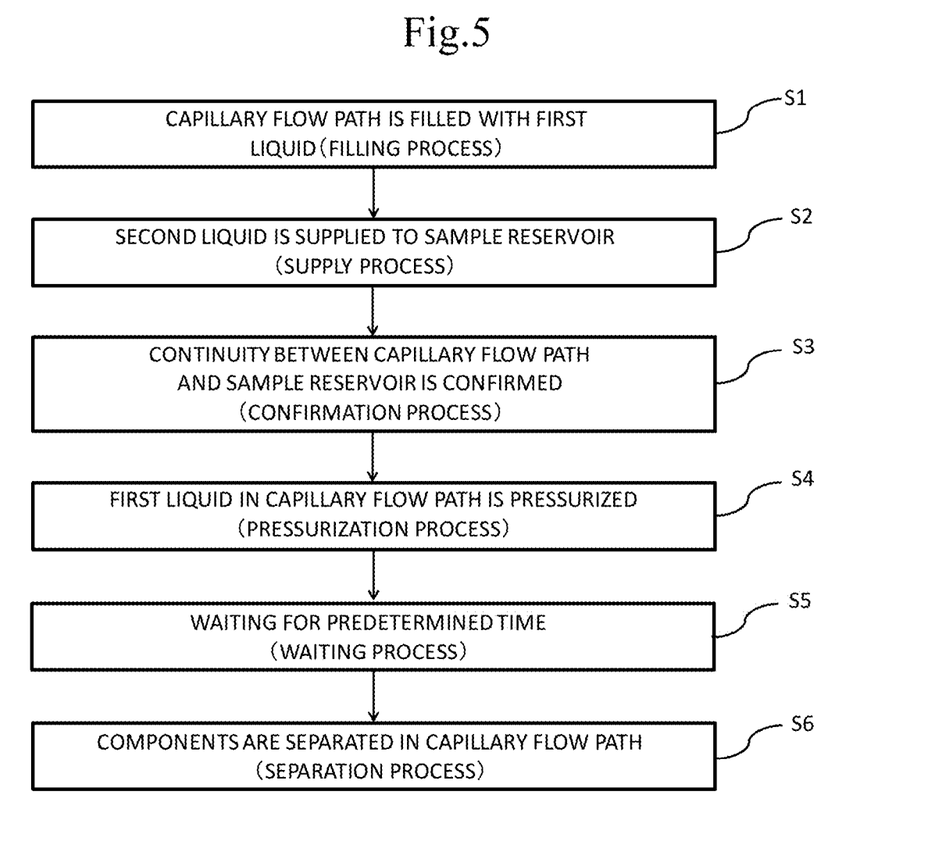
FIG. 5 is a flow chart showing a variation of the analysis method of a mode of the present invention.

It is desirable that only the portion of the second liquid having moved into the capillary flow path 2 theoretically determined based on the voltage application condition in the confirmation process (S3), the size of the capillary flow path 2, etc. is sent back to the sample reservoir 1 in the pressurization process (S4). However, due to an individual difference in the microchip 100, and conditions such as environmental temperature, it is difficult to send back accurately only the portion of the second liquid having moved into the capillary flow path 2 to the sample reservoir 1. Therefore, it is preferable to send back the second liquid and the first liquid in the vicinity of the boundary together toward the sample reservoir 1 in the pressurization process (S4). Since the volume of the capillary flow path 2 is very small compared to the volume of the sample reservoir 1, a very small amount of the first liquid is transferred into the sample reservoir 1. The very small amount of the first liquid transferred into the sample reservoir 1 is diluted by the large amount of the second liquid present in the sample reservoir 1. Furthermore, since the volume of the capillary flow path 2 is very small, and there remains a fluid flow from the capillary flow path 2 to the sample reservoir 1 due to pressurization, the second liquid present in the section sample reservoir 1 is prohibited from moving to the capillary flow path 2, an interface between the first liquid and the second liquid can be formed at the opening of the capillary flow path 2 in the connecting portion 1 between the sample reservoir 1 and the capillary flow path 2.

When the second liquid and the first liquid near the boundary are sent back together to the sample reservoir 1 in the pressurization process (S4), depending on the degree of backward transfer of the first liquid near the boundary to the sample reservoir 1, the waiting time in the waiting process (S5) described later should be changed. For example, in a case where a relatively large amount of the first liquid near the boundary is sent back toward the sample reservoir 1, it is preferable to secure a longer waiting time.

(Waiting Process)

The analysis method of the aspect includes a waiting process (S5) of waiting for a predetermined time after the pressurization process (S4) and before the separation process (S6) described later. The waiting time is preferably, for example, from 0.1 sec to 10 sec, and more preferably from 0.2 sec to 3 sec. By this means, even when the first liquid moves toward the sample reservoir 1, it can be diluted with a large amount of the second liquid present in the sample reservoir 1, and an interface between the first liquid and the second liquid can be formed at the opening of the capillary flow path in the connecting portion 1 between the sample reservoir 1 and the capillary flow path 2. However, since there is a risk of occurrence of a phenomenon that the second liquid flows back again into the capillary flow path 2 from the sample reservoir 1, the waiting time should be preferably short enough to avoid such a phenomenon.

The volume of the first liquid to be sent back to the sample reservoir 1 in the pressurization process (S4) is preferably at a level allowing dilution with the second liquid in the sample reservoir 1 after the lapse of the waiting time in the waiting process (S5). For example, the volume ratio of the total amount of the liquids (the first liquid and the second liquid) sent back to the sample reservoir 1 in the pressurization process (S4) to the amount of the second liquid supplied to the sample reservoir 1 in the supply process (S2) (total amount of the liquids to be sent back/amount of the second liquid supplied to the sample reservoir 1) is required to be from 0.0001 to 0.1. Alternatively, the volume ratio of the total amount of the liquids sent back to the sample reservoir 1 in the pressurization process (S4) to the volume of the capillary flow path 2 (total amount of the liquids to be sent back/volume of the capillary flow path 2) is required to be from 0.1 to 100.

(Separation Process)

Next, a variation of the analysis method includes a separation process (S6) after the waiting process (S5). Since the separation process (S6) is similar to the above-described separation process (S5), the description thereof will be omitted.

[Kit]

The microchip used in this aspect may be combined with a cartridge storing a liquid for analysis to form a kit. The above kit may include, for example, a microchip and cartridges for storing respectively a diluent and a first liquid used in the aspect.

[Analysis System]

The analysis system of the aspect includes an arrangement unit in which a microchip provided with a capillary flow path, and a sample reservoir connected to the capillary flow path is arranged; a filling means for filling the capillary flow path in the microchip arranged in the arrangement unit with a first liquid for electrophoresis; a supply means for supplying a second liquid containing a sample into the sample reservoir in the microchip arranged in the arrangement unit;

a control unit for controlling pressurization of the first liquid into the capillary flow path from a side of the capillary flow path that is opposite from the side connected to the sample reservoir, the pressurization being conducted after the filling with the first liquid by the filling means and after the supply of the second liquid by the supply means; and a separation means by which, after pressurizing the first liquid into the capillary flow path, a voltage is applied between the sample reservoir storing the second liquid and the capillary flow path filled with the first liquid, such that components in the sample contained in the second liquid move through the capillary flow path and the components are separated in the capillary flow path. The analysis system of the aspect is a mode of the analysis system used to perform the above-described analysis method of the aspect, and is superior in sample analysis accuracy.

The analysis system of the aspect includes an arrangement unit in which the microchip described above is arranged. The microchip arranged in the arrangement unit includes, for example, a sample reservoir, a capillary flow path connected to the sample reservoir, and the like. The microchip may also include an electrophoresis liquid reservoir connected to the capillary flow path on the side opposite to the sample reservoir. By the filling means, the capillary flow path is filled with the first liquid. When a microchip provided with the electrophoresis liquid reservoir is used, the first liquid for electrophoresis is supplied to the electrophoresis liquid reservoir by the filling means, and the first liquid is supplied into the capillary flow path for filling it by pressurization. Also, the second liquid is supplied by a supply means to the sample reservoir and stored in it. As the filling means and the supply means, for example, a pump described later may be used.

In the analysis system of this aspect, the control unit controls pressurization on the first liquid into the capillary flow path in a microchip in which the capillary flow path is filled with the first liquid and the second liquid is stored in the sample reservoir. By this means, an interface between the first liquid and the second liquid may be formed similar to the analysis method described above, and by applying a voltage in a state where the interface is formed, a sample can be analyzed with high accuracy. As the method of pressurizing the first liquid into the capillary flow path, a method by which the first liquid is pressurized by air pressure into the capillary flow path, and the second liquid having moved into the capillary flow path is sent back to the sample reservoir 1 may be applied. A filling means may serve both as a constituent for pressurizing the first liquid into the capillary flow path to fill it, and as a constituent for pressurizing the first liquid to be resupplied into the capillary flow path. Alternatively, a constituent in which the first liquid is pressurized to be resupplied into the capillary flow path by a pressurization means different from the filling means may be applied.

Further, the analysis system of this aspect separates components in the capillary flow path with the separation means by applying a voltage between the sample reservoir storing the second liquid and the capillary flow path filled with the first liquid after pressurization on the first liquid into the capillary flow path such that components in a sample contained in the second liquid move in the capillary flow path. The separation means applies a predetermined voltage to the inside of the capillary flow path, and includes, for example, an anode to be inserted into the sample reservoir, a cathode to be inserted into the electrophoresis liquid reservoir, and a voltage application means for applying a voltage between the anode and the cathode.

The analysis system of this aspect may include a confirmation means for confirming the continuity between the capillary flow path filled with the first liquid and the sample reservoir storing the second liquid after filling with the first liquid by the filling means and after supplying the second liquid by the supply means, but before pressurizing the first liquid in the capillary flow path. The aforementioned voltage application means may also serve as the confirmation means.

The analysis system of the aspect may be provided with a detection means for detecting the above separated components. For example, the detection means may detect the separated components by an optical method such as an absorbance measurement. For example, a light emitting unit and a measurement unit may be used as the detection means.

For example, the light emitting unit emits light for measuring the absorbance and is a unit that irradiates the detector of a microchip with light. The light emitting unit includes, for example, an LED chip that emits light with a wavelength in a predetermined range, an optical filter, a lens, and the like. The light emitting unit may have a slit.

For example, the measurement unit is a unit that receives light having irradiated the detector of the microchip, and measures the absorbance. The measurement unit is provided with, for example, a photodiode, a photo IC, or the like.

Further, the analysis system of the aspect may be provided with a diluent tank, an electrophoresis liquid tank, a pump, and the like. It may be so configured that the filling means, the supply means, the separation means such as the voltage application means, the detection means such as a light emitting unit and a measurement unit, and the like are controlled by the control unit. Also, the control unit may control the filling means or the pressurizing means to pressurizes the first liquid to be resupplied into the capillary flow path, and thereafter after waiting for a predetermined time period control the separation means to make components in a sample contained in the second liquid move into the capillary flow path to be separated in the capillary flow path.

The diluent tank is, for example, a tank for storing a diluent for diluting a sample. For example, after mixing a diluent supplied from the diluent tank and a sample in a mixing tank, a liquid (second liquid) obtained by diluting the sample may be supplied to the sample reservoir. In this case, a microchip used in the analysis system of the aspect may include a mixing tank for mixing the diluent supplied from the diluent tank and the sample containing an analyte.

The electrophoresis liquid tank is, for example, a tank for storing a first liquid for electrophoresis to be supplied to the electrophoresis liquid reservoir.

Figure 2:
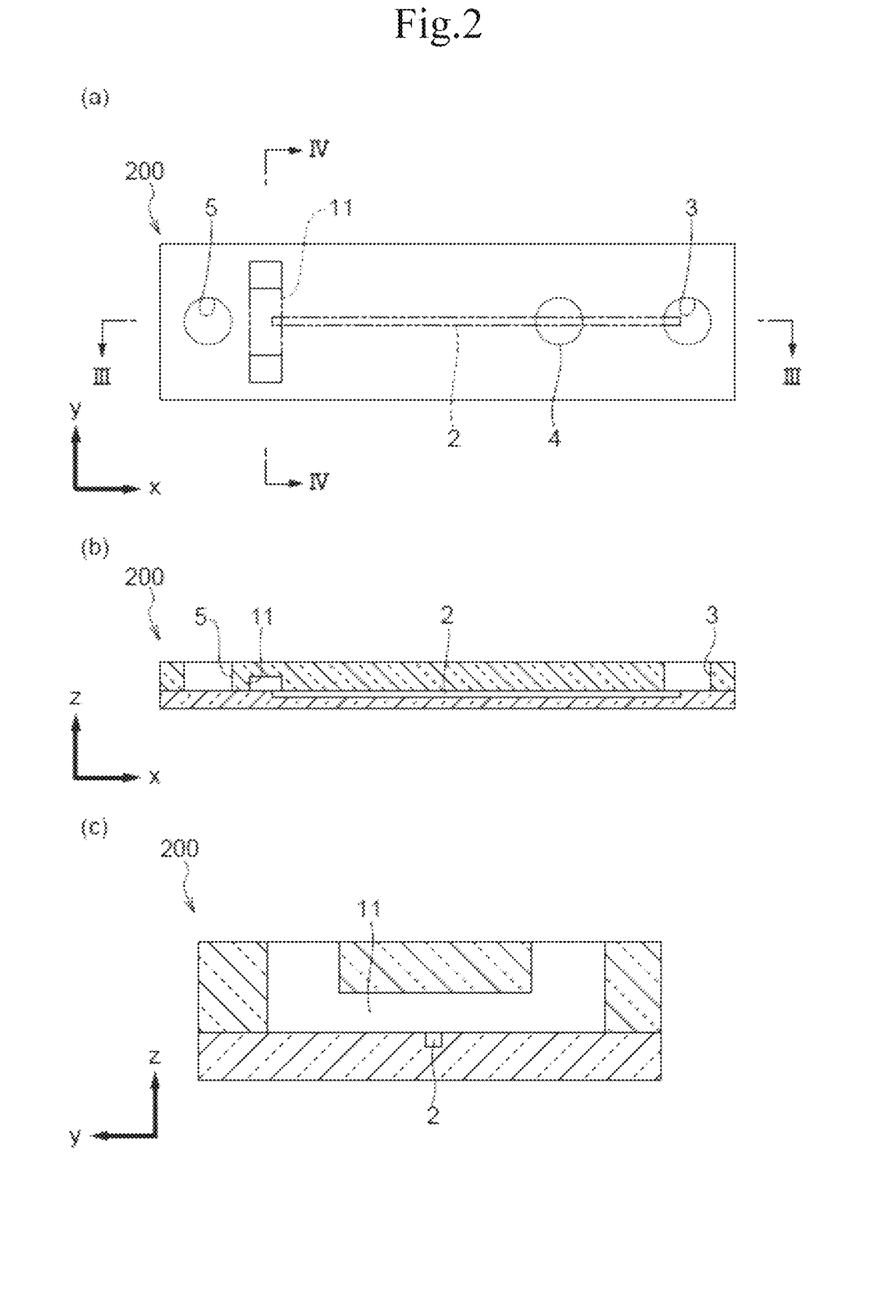
FIG. 2 shows schematic configuration diagrams of a microchip used in the analysis system of an aspect of the invention, and (a) is a top view, (b) is a sectional view taken along the line in (a), and (c) is a sectional view taken along the line IV-IV of (a).

The pump is, for example, a unit for supplying a diluent to a mixing tank by pressure application, or supplying a first liquid to an electrophoresis liquid reservoir by pressure application, and filling a capillary flow path with the first liquid. A liquid (second liquid) obtained by diluting a sample containing an analyte in the mixing tank may be supplied to a sample reservoir by the pump. The second liquid stored in the sample reservoir may be made to flow by performing once at least one of discharge and suction using the pump, or by repeating discharge and suction using the pump. In addition, the second liquid may be made to flow after confirmation of the continuity between the capillary flow path filled with the first liquid and the sample reservoir storing the second liquid by a confirmation means such as a voltage application means, FIG. 2 shows a microchip provided with a mixing tank and having a structure capable of allowing a second liquid stored in a sample reservoir to flow. The microchip 200 shown in FIG. 2 includes a mixing tank 5 for mixing a diluent with a sample containing an analyte and a sample reservoir 11 including two openings and capable of allowing the second liquid to flow. When allowing the second liquid stored in the sample reservoir 11 to flow, for example, at least one of discharge and suction using the pump may be performed once on the second liquid stored in the sample reservoir 11, or alternatively discharge and suction using the pump may be repeated to make it reciprocate in the y direction in FIG. 2.

In the case of allowing the second liquid stored in the sample reservoir 11 to flow by repeating discharge and suction using the pump, it is preferable that, after the pump is strongly idled, the pump is connected to the sample reservoir 11 of the microchip 200 to flow the second liquid stored in the sample reservoir 11. This makes it easier to stabilize the pressure during pump operation.

It is enough for the control unit insofar as it controls pressurization on the first liquid into the capillary flow path after the filling with the first liquid by a filling means, and after the supply of the second liquid by a supply means. Also it is enough for the control unit, insofar as it controls each of the aforedescribed constituents in the analysis system, for example it is enough insofar as it controls each of the constituents such that each of the aforedescribed constituents in the analysis system carry out each of the processes shown in FIG. 4 in the specified order. The control unit is provided with, for example, CPU, a memory, and an interface.

Figure 3:
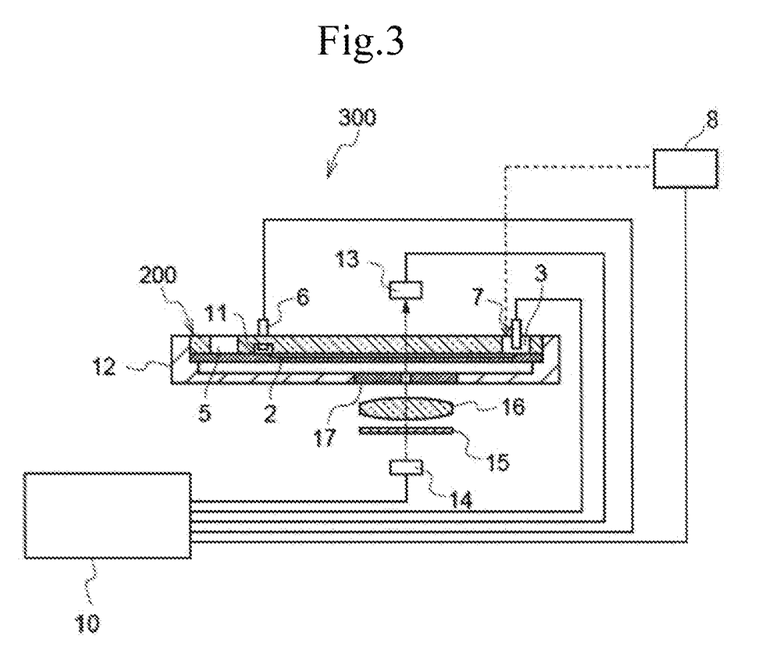
FIG. 3 is a sectional view showing a schematic configuration of the analysis system of an aspect of the invention.

The analysis system of the aspect will be described with reference to FIG. 3. FIG. 3 is a sectional view showing a schematic configuration of an analysis system of one aspect of the invention. The analysis system 300 shown in FIG. 3 includes an arrangement unit 12 in which a microchip 200 is arrange, an anode 6, a cathode 7, a pump 8, a control unit 10, a photodiode 13, an LED chip 14, an optical filter 15, a lens 16, and a slit 17.

The anode 6 is inserted into the sample reservoir 11, and the cathode 7 is inserted into the electrophoresis liquid reservoir 3. The LED chip 14 irradiates a detector 4 of the microchip 200 with light, and the photodiode 13 receives the light having impinged the detector 4 of the microchip 200, and measures the absorbance.

The pump 8 supplies the first liquid to the electrophoresis liquid reservoir 3 and then supplies by pressurization the first liquid into the capillary flow path 2 to fill the same, and further resupply by pressurization the first liquid into the capillary flow path 2 before separation of components in the capillary flow path by voltage application.

The control unit 10 controls each constituent in the analysis system 300, and may perform, for example, a control of filling and resupplying of the first liquid by a filling means 8, a control of a voltage applied to an anode 6 and a cathode 7, a control of light emitted from a LED chip 14, a measurement of the absorbance with respect to the light received by a photodiode 13, or the like. Also, the control unit 10 may perform a control of discharge and suction of the pump, a control of supply or flow of a diluent, a second liquid, etc., or the like. The control unit 10 may be so configured to control pressurization on the first liquid by a pressurizing means different from that for the filling means 8.

Although the analysis method and the analysis system according to one aspect of the invention have been described above, the invention is not limited to these aspects and various improvements, changes, and modifications may be made based on knowledge of those skilled in the art without departing from the spirit of the invention. The items described in the items of the analysis method and the analysis system according to one aspect of the invention may be combined as appropriate.

EXAMPLES

Next, one aspect of the invention will be described based on the following Examples, but the invention is not limited to the following Examples.

Example 1

<Preparation of Microchip>

In this Example, a microchip in which each constituent satisfied the following conditions was prepared. The inner wall of the capillary flow path is covered with poly(diallyldimethylammonium chloride) (PDADMAC, produced by Sigma-Aldrich, Inc.).

Sample reservoir Capacity 20 μL
Electrophoresis liquid reservoir Capacity 10 μL
Capillary flow path Depth 0.04 mm×width 0.04 mm×length 30 mm (Optical detection is performed by a detector positioned 20 mm away from the end on the side of the sample reservoir)

<Preparation of First Liquid and Second Liquid>

A first liquid was prepared using 40 mM citric acid, 1.25% (w/v) sodium chondroitin sulfate C, 0.1% (w/v) LS-110 (produced by Kao Corporation), and 0.1% (w/v) sodium azide, and used after adjustment to pH 5.0 with dimethylaminoethanol (for pH adjustment).

As a sample, 95 μL of whole blood collected from a human body was used.

A diluent was prepared using 40 mM citric acid, 1.0% (w/v) sodium chondroitin sulfate C, 500 mM NDSB-201 (produced by Anatrace), 0.1% (w/v) LS-110 (produced by Kao Corporation), and 0.1% (w/v) sodium azide, and used after adjustment to pH, and used after adjustment to pH 6.0 with dimethylaminoethanol (for pH adjustment).

The sample was diluted 41-fold with the diluent to prepare a second liquid.

<Implementation of Capillary Electrophoresis>

An analysis of hemoglobin in the sample was conducted according to the following procedure.

1) A microchip was set in a dedicated device manufactured by ARKRAY, Inc.

2) The first liquid was added to the electrophoresis liquid reservoir, and supplied by pressurization into the capillary flow path to fill it.

3) The second liquid was added to the sample reservoir.

4) An anode was brought into contact with the sample reservoir and a cathode was brought into contact with the electrophoresis liquid reservoir, to which a voltage of about 3000 V was applied, and flow of a current of 5 μA or more was confirmed.

5) The second liquid stored in the sample reservoir was made to flow through discharge of a pump.

6) The first liquid stored in the electrophoresis liquid reservoir was pressurized under the condition of 6 kPa for 1 sec to resupply the first liquid into the capillary flow path.

7) The anode was brought into contact with the sample reservoir and the cathode was brought into contact with the electrophoresis liquid reservoir, and electrophoresis was started under a constant current control of 70 μA at a voltage of about 1500 V.

8) The absorbance at 415 nm was measured by a detector to obtain an electropherogram. The electrophoresis was performed for 35 sec.

Example 2

The electrophoresis was performed in the same manner as in Example 1 except that at the step 6 of the above <Implementation of Capillary Electrophoresis> the first liquid stored in the electrophoresis liquid reservoir was pressurized under the condition of 10 kPa and 1 sec to resupply the first liquid into the capillary flow path.

Comparative Example 1

The electrophoresis was performed in the same manner as in Example 1 except that the step 6 of the above <Implementation of Capillary Electrophoresis> was not performed.

Figure 6A:
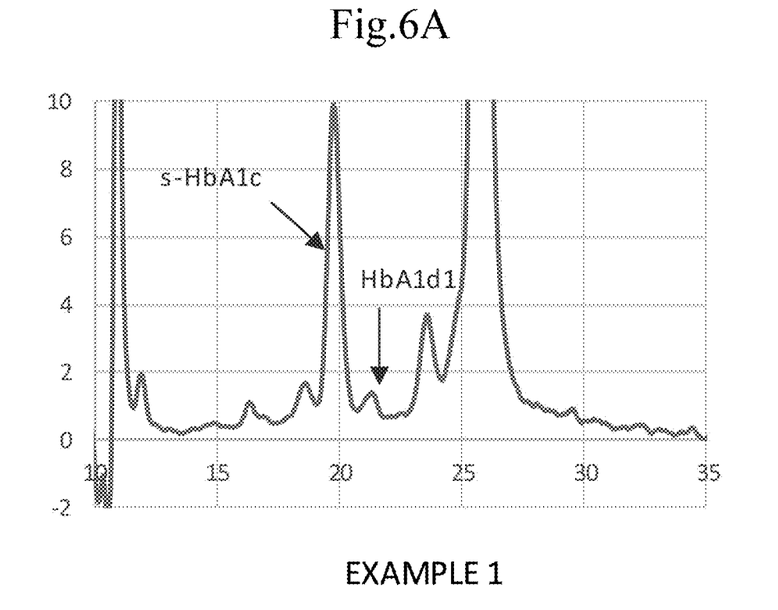
FIG. 6A is graphs showing results of electrophoresis using the microchip in example 1.
Figure 6B:
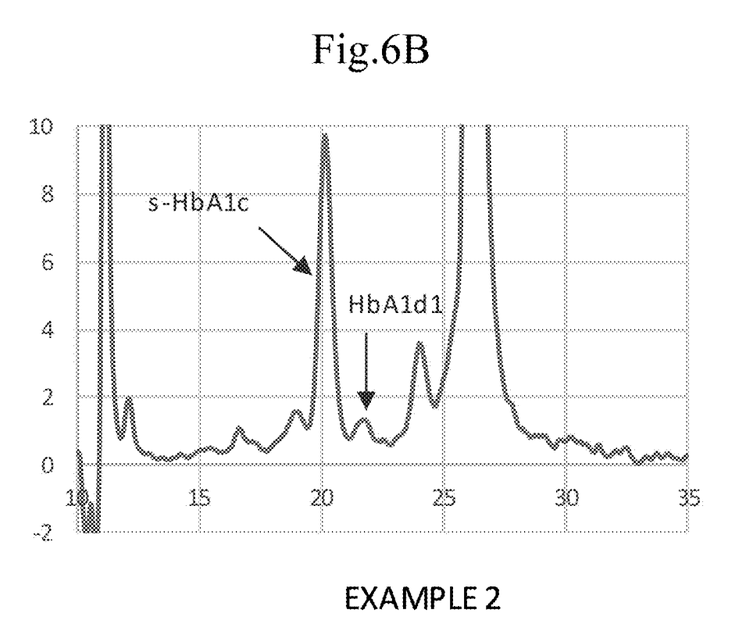
FIG. 6B is graphs showing results of electrophoresis using the microchip in example 2.
Figure 6C:
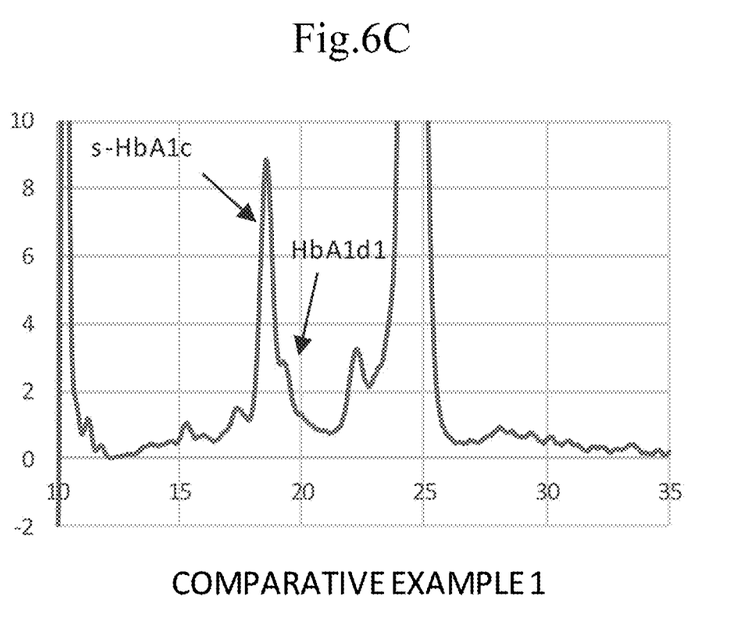
FIG. 6C is graphs showing results of electrophoresis using the microchip in comparative example 1.

The results of the capillary electrophoresis in Examples 1 and 2, and Comparative Example 1 are as shown in FIGS. 6A, 6B and 6C. In FIGS. 6A, 6B and 6C, the abscissa represents detection time (sec), and the ordinate represents the amount of change in absorbance (mAbs/sec). As shown in FIGS. 6A and 6B, in the electropherograms of Example 1 and Example 2 the peaks of s-HbA1c and HbA1d1, which were analyte components, appeared separately and clearly at time points different from each other. On the other hand, as shown in FIG. 6C, in the electropherogram of Comparative Example 1, the peaks of s-HbA1c and HbA1d1, which were analyte components, did not appear separately and clearly. Therefore, the analysis methods of Example 1 and Example 2 were superior in the analysis accuracy with respect to the sample compared to the analysis method of Comparative Example 1.

DESCRIPTION OF SYMBOLS

1, 11: Sample reservoir, 2: Capillary flow path, 3: Electrophoresis liquid reservoir, 4: Detector, 5: Mixing tank, 6: Anode, 7: Cathode, 8: Pump (filling means), 10: Control unit, 12: Arrangement unit, 13: Photodiode (measurement unit), 14: LED chip (light emitting unit), 15: Optical filter, 16: Lens, 17: Slit, 100, 200: Microchip, 300: Analysis system

What is claimed is:

1. An analysis method using a microchip that is provided with a capillary flow path and a sample reservoir connected to the capillary flow path, wherein the capillary flow path is configured to be filled with a first liquid for electrophoresis, and the sample reservoir is configured to store a second liquid containing a sample, the analysis method comprising:
    a filling process of filling the capillary flow path with the first liquid;
    a supply process of supplying the second liquid to the sample reservoir;
    a confirmation process of applying a first voltage between the sample reservoir and the capillary flow path so as to confirm continuity between the capillary flow path filled with the first liquid and the sample reservoir storing the second liquid, wherein the confirmation process is performed until a predetermined current is 5 µA or more;
    after the confirmation process, a pressurization process of pressurizing the first liquid into the capillary flow path from a side of the capillary flow path that is opposite a side connected to the sample reservoir so that the first liquid is supplied to the capillary flow path; and
    after the pressurization process, a separation process of applying a second voltage between the sample reservoir storing the second liquid and the capillary flow path filled with the first liquid, such that an electroosmotic flow from the sample reservoir to the capillary flow path occurs, components in the sample contained in the second liquid move in the capillary flow path, and the components are separated in the capillary flow path.

2. The analysis method according to claim 1, wherein, in the confirmation process, the components in the sample move in the capillary flow path.

3. The analysis method according to claim 2, wherein an interface between the first liquid and the second liquid is formed in a connecting portion between the capillary flow path and the sample reservoir by pressurizing the first liquid into the capillary flow path in the pressurization process.

4. The analysis method according to claim 1, wherein an interface between the first liquid and the second liquid is formed in a connecting portion between the capillary flow path and the sample reservoir by pressurizing the first liquid into the capillary flow path in the pressurization process.

5. The analysis method according to claim 1, wherein the components included in the sample include a biologically derived substance.

6. The analysis method according to claim 1, wherein
    a volume ratio of an amount of the first liquid supplied to the capillary flow path from the side opposite the side connected to the sample reservoir in the pressurization process to an amount of the second liquid supplied to the sample reservoir in the supply process (amount of the first liquid supplied to the capillary flow path/amount of the second liquid supplied to the sample reservoir) is from 0.0001 to 0.1, or,
    a volume ratio of the amount of the first liquid supplied to the capillary flow path from the side opposite the side connected to the sample reservoir in the pressurization process to the volume of the capillary flow path (amount of the first liquid supplied to the capillary flow path/volume of the capillary flow path) is from 0.1 to 100.

7. The analysis method according to claim 1, wherein
    a volume ratio of an amount of the first liquid supplied to the capillary flow path from the side opposite the side connected to the sample reservoir in the pressurization process to an amount of the second liquid supplied to the sample reservoir in the supply process (amount of the first liquid supplied to the capillary flow path/amount of the second liquid supplied to the sample reservoir) is from 0.0001 to 0.1.

8. The analysis method according to claim 1, wherein
    a volume ratio of an amount of the first liquid supplied to the capillary flow path from the side opposite the side connected to the sample reservoir in the pressurization process to a volume of the capillary flow path (amount of the first liquid supplied to the capillary flow path/volume of the capillary flow path) is from 0.1 to 100.

9. The analysis method according to claim 1, wherein the sample includes blood.

10. The analysis method according to claim 1, wherein the components include hemoglobin.

11. The analysis method according to claim 10, wherein the hemoglobin includes glycated hemoglobin.

12. The analysis method according to claim 1, further comprising a waiting process after the pressurization process and before the separation process, the waiting process includes waiting for 0.1 second to 10 seconds.

13. The analysis method according to claim 12, wherein the waiting process includes waiting for 0.2 second to 3 seconds.

14. The analysis method according to claim 1, wherein the separation process is performed under a constant current.

15. The analysis method according to claim 1, wherein at least one of the first voltage and the second voltage is in a range of 0.5 kV to 20 kV.

16. The analysis method according to claim 1, wherein at least one of the first voltage and the second voltage is in a range of 0.5 kV to 10 kV.

17. The analysis method according to claim 1, wherein at least one of the first voltage and the second voltage is in a range of 0.5 kV to 5 kV.

18. The analysis method according to claim 1, wherein, in the pressurization process, the first liquid is supplied to the side of the capillary flow path that is opposite the side connected to the sample reservoir so that the first liquid reaches the sample reservoir.

\* \* \* \* \*